United States Patent [19]

Novák

[11] Patent Number: 4,880,630

[45] Date of Patent: Nov. 14, 1989

[54] SKIN CARE COMPOSITIONS HAVING KERATOLYTIC AND ANTIINFLAMMATORY ACTIVITY

[75] Inventor: Tibor Novák, Lakitelek, Hungary

[73] Assignee: Innofinance Altalanos Innovacios Penzintezet, Budapest, Hungary

[21] Appl. No.: 105,229

[22] PCT Filed: Dec. 20, 1985

[86] PCT No.: PCT/HU85/00076

§ 371 Date: Aug. 7, 1987

§ 102(e) Date: Aug. 7, 1987

[87] PCT Pub. No.: WO87/03803

PCT Pub. Date: Jul. 2, 1987

[51] Int. Cl.⁴ ............................................. A61K 35/78
[52] U.S. Cl. .................................................. 424/195.1
[58] Field of Search ...................................... 424/195.1

[56] References Cited

PUBLICATIONS

Codex Vegetabilis, E. F. Steinmetz, 1957, No. 677.
Chemical Abstracts, 107(14):120844c, Phytochemical Study on The Leaves of Lycium Halimifolium, 1987.
C.A., 107(7):55789x, Phytochemical Study on The Leaves of Lycium Halimifolium, 1987.
C.A., 101(19):167206n, Search for Alkaloid-Type Bases in Lycium Halimifolium, 1984.

Primary Examiner—William R. Dixon, Jr.
Assistant Examiner—E. McAvoy
Attorney, Agent, or Firm—Herbert Dubno; Jonathan Myers

[57] ABSTRACT

The invention relates to skin care compositions having keratolytic and antiinflammatory activity comprising the extract of the leaf, green stalk and/or flower of *Lycium halimifolium* as active ingredient.

8 Claims, No Drawings

SKIN CARE COMPOSITIONS HAVING KERATOLYTIC AND ANTIINFLAMMATORY ACTIVITY

The invention relates to skin care compositions having keratolytic and antiinflammatory activity.

BACKGROUND OF THE INVENTION

Recently more and more so called phytocosmetic skin care compositions have been put on the market which contain plant extracts as active ingredients.

The object of the present invention is to find new active ingredients of plant origin for the use in skin care compositions.

The plant *Lycium halimifolium* belongs to the Lycium genus. It is native to the basin of the Mediterranean Sea, in Hungary it grows wild. The various Lycium species have several names, in many instances it is difficult to discern the individual species.

In the last two decades, mainly during the early seventies *Lycium chinense* and *Lycium europeum* are mentioned in the literature. A great part of the references relate to the various components of the Lycium species (C.A., 62, 3064g, 1965; Vopr. Farm., 1, 49–51, 1973; Phytochem., 15, 1701–2, 1976; Syoyakugaku Zasshi, 17, 14–15, 1963, and 20, 481–4, 1969; C.A., 65, 19224f, 1969; Arch. Pharm. 310-1, 35–40, 1977, and 308-8, 653–54, 1975; Pak. J. Sci. Ind. Res., 11-3, 247–49, 1968; Annales Inst. Sup. di Sanita, Roma, 5, 51–53, 1969; Curr. Sci., 50-5, 235, 1981). In other references the physiological properties of Lycium species are discussed. Osawa and Nunokawa (Niigatu Igakkai Zasshi, 83-2, 82–92, 1969, Nippon Naibumpi Gakkai Zasshi, 46-1, 32–52, 1972) investigated the effect of the extracts prepared from the crop, leaf and root of *Lycium chinense* on the ovulation of rabbits. Sanwa isolated a protein from the aqueous extract of *Lycium chinense* which reduces the cholesterol level of blood (C.A., 94, 71477n, 1981; Kokai 80, 160 723). A compound named cucoamine was isolated from *Lycium chinense* by Japanese researchers which has a significant blood pressure reducing activity (Tetrahedron Letters, 1355–6, 1980). Also the role of *Lycium chinense* in therapy is mentioned by the authors, accordingly it is used in the East for reducing the blood-sugar level and for antipyresis and its use against stress and ulcus is described as well. According to the investigations of Lapirina (Farmatsevt. Zh., 19-4, 52–8, 1964) in animal tests by the use of the extract of *Lycium halimifolium* a long-lasting blood-sugar reducing effect can be achieved. According to the GB patent specifications 1 157 717 and 1 300 966 pharmaceutically active evaporation residue and liquid distillate can be produced by the vacuum distillation of the extracts of plant species, e.g. of *Lycium chinense*. An apparatus is described for carrying out the process but the specifications do not contain any pharmacological data. GB patent specification 1 106 133 relates to a process for the recovery of saponines from plant tissues, e.g. from *Lycium barbarum*. The saponines thus obtained are suitable for treating malignant and non-malignant tumors and Trichomonas infections. However, there is no reference in the literature of the keratolytic and antiinflammatory activity of any of the Lycium species, such as of *Lycium halimifolium*. Furthermore there is no reference in the literature to any skin care composition having the above activity.

BRIEF DESCRIPTION OF THE INVENTION

During our experiments it has been surprisingly found that by the extraction of the leaf, green stalk and/or flower of *Lycium halimifolium* an active ingredient solution was obtained which was excellently suitable for the local treatment of keratinized skin, e.g. for the extirpation of verrucae and for calming the inflamed skin when admixed with diluents and/or vehicles and optionally with other known substances used in the cosmetic industry, e.g. propolis.

DETAILED DESCRIPTION OF THE INVENTION

The present invention relates to skin care compositions having keratolytic and antiinflammatory activity comprising the extract of the leaf, green stalk and/or flower of *Lycium halimifolium* as active ingredient together with the usual vehicles and/or diluents.

The extract is prepared from the dried and crushed plant with water or with a mixture of water and a water miscible organic solvent, preferably with a mixture of ethanol and water by steeping or boiling. After filtering the extract the solution of the active ingredient is formulated directly or after lyophilization with the usual cosmetic vehicles and/or diluents (e.g. vegetable oils) into cosmetic compositions, e.g. into creams, solutions, gels, body powders etc.

The compositions of the invention show new favorable effects.

The gel (Example 12) and the solution (Example 11) were examined on 90 women and 45 men aged from 5 to 45 years having verrucae on the palm or sole (*Verrucae vulgaris*). A group of 35 women and 15 men aged from 4 to 40 years served as control group, this group was treated with a composition comprising 2.0 g of salicylic acid, 2.0 g of lactic acid, 1.0 g of diethyl ether and 5.0 g of collodium, generally used for the treatment of verrucae. The treatment was carried out twice daily in both groups by applying the compositions to the verrucae, in the evening after the second treatment a bandage was applied. The tensive, inflammatory symptoms of the skin treated with the composition of the invention already on the third day of the treatment were improving, the desquamation of the skin has begun. After a 7-week treatment in 110 cases the verrucae disappeared, in 25 cases improvement was observable. During the treatment no allergic reaction, irritative dermatitis or hypersensitivity were observed. In the control group after the 7-week treatment the verrucae only in 5 cases disappeared.

The following non-limitative Examples show the compositions of the invention and the preparation of the active ingredient.

EXAMPLE 1

Leaves and green stalks of *Lycium halimifolium* were dried at 20° C. in a manner usual for herbs, then crushed. 1 kg of the crushed substance was boiled for 2 hours in 10 liters of deionized water, the resulting extract was filtered and the filtrate was stored in a dry, cool place until use.

EXAMPLE 2

Leaves and green stalks of *Lycium halimifolium* were dried as in Example 1, then crushed. 1 kg of the crushed substance was boiled for 20 minutes in 8 liters of water, the resulting extract was filtered and the filter cake (drug residue) was pressed with a hydraulic press. The drug was again extracted in the same way with 4 liters of water, the aqueous extracts were combined, filtered and lyophilized. 258 g of dry extract were obtained.

EXAMPLE 3

Leaves and green stalks of *Lycium halimifolium* were dried as in Example 1, then crushed, 1 kg of the crushed substance was steeped for 36 hours in 5.0 liters of 70% by vol. aqueous ethanol. Then the extract was filtered and stored in a dry, cool place until use.

EXAMPLE 4

Leaves, green stalks and flowers of *Lycium halimifolium* were dried as in Example 1, then crushed. 1 kg of the crushed substance was boiled for 20 minutes in 5 liters of water, the extract was filtered and stored in a dry, cool place until use.

EXAMPLE 5

Flowers of *Lycium halimifolium* were dried as in Example 1, then crushed. 1 kg of the crushed substance was steeped for 12 hours at room temperature in 5 liters of deionized water. The extract was filtered and stored in a dry, cool place until use.

EXAMPLE 6

| Skin care cream | |
|---|---|
| Components | |
| Extract of Example 1 | 20.00 g |
| sodium laurylsulfate | 1.00 g |
| Nipagine | 0.10 g |
| adeps lanae | 7.00 g |
| vaselinum album | 7.00 g |
| oleum helianti | 3.00 g |
| oleum ricini | 3.00 g |
| glycerol | 5.00 g |
| deionized water | 53.80 g |
| geranium oil | 0.10 g |

The components, excluding the active ingredient and geranium oil, are mixed, the mixture is molten on a water bath, heated to the boiling point, then cooled under constant stirring, the water evaporated in the course of heating is supplemented. The active ingredient and geranium oil are added to the mixture in small portions and the mixture is homogenized.

EXAMPLE 7

| Skin care cream | |
|---|---|
| Components | |
| Extract of Example 2 | 2.65 g |
| sodium laurylsulfate | 1.00 g |
| Nipagine | 0.10 g |
| adeps lanae | 7.00 g |
| vaselinum album | 7.00 g |
| oleum helianti | 3.00 g |
| oleum ricini | 3.00 g |
| glycerol | 5.00 g |
| propolis | 0.11 g |
| geranium oil | 0.24 g |
| deionized water | 71.00 g |

The cream is prepared according to Example 6.

EXAMPLE 8

| Skin care cream | |
|---|---|
| Components | |
| Extract of Example 5 | 5.00 g |
| sodium laurylsulfate | 1.00 g |
| Nipagine | 0.10 g |
| adeps lanae | 7.00 g |
| vaselinum album | 7.00 g |
| oleum helianti | 3.00 g |
| oleum ricini | 3.00 g |
| glycerol | 5.00 g |
| geranium oil | 0.10 g |
| deionized water | 68.80 g |

The cream is prepared according to Example 6.

EXAMPLE 9

| Body lotion | |
|---|---|
| Components | |
| Extract of Example 1 | 95.00 g |
| Nipagine | 0.10 g |
| glycerol | 4.50 g |
| geranium oil | 0.40 g |

Nipagine, then glycerol and geranium oil are added to the extract of Example 1, the mixture is homogenized, sterilized by filtration and filled into ampoules or flasks under sterile conditions or it is formulated by means of a propellant into spray form.

EXAMPLE 10

| Body lotion | |
|---|---|
| Components | |
| Extract of Example 3 | 50.00 g |
| Nipagine | 0.20 g |
| sodium laurylsulfate | 0.05 g |
| glycerol | 4.45 g |
| deionized water | 45.20 g |
| geranium oil | 0.10 g |

The solid components are dissolved in the deionized water, glycerol and geranium oil are added to the solution, the solution is homogenized, sterilized by filtration and it is formulated according to Example 9.

EXAMPLE 11

| Body lotion | |
|---|---|
| Components | |
| Extract of Example 4 | 5.00 g |
| Nipagine | 0.10 g |
| glycerol | 5.00 g |
| geranium oil | 0.10 g |
| deionized water | 89.80 g |

Deionized water is homogenized with glycerol and Nipagine, the extract of Example 4 is added thereto, finally geranium oil is added, the solution is homogenized, sterilized by filtration and formulated according to Example 9.

EXAMPLE 12

Gel

| Components | |
|---|---|
| Extract of Example 1 | 50.00 g |
| Carbopol 940 (gel forming polymer) | 2.00 g |
| propylene glycol | 10.00 g |
| sodium hydroxide | 0.10 g |
| Nipagine | 0.10 g |
| geranium oil | 0.10 g |
| deionized water | 37.70 g |

The extract of Example 1 is mixed with the deionized water, propylene glycol and Nipagine, then Carbopol 940 is added to the above mixture. It is allowed to swell for 10 hours, then it is homogenized, sodium hydroxide is added under stirring to the homogenizate in the form of a 10% aqueous solution, finally geranium oil is added and the mixture is homogenized.

EXAMPLE 13

A gel is prepared according to Example 12 with the exception that as active ingredient 50.00 g of the extract of Example 4 is used.

EXAMPLE 14

Body powder 4.5 g of the extract of Example 2 are homogenized with 95.25 g of talc and 0.25 g of menthol. The mixture is sterilized by UV radiation, then it is formulated under sterile conditions.

I claim:

1. A skin care composition in the form of a cream, body lotion, topical gel, or body powder having keratolytic and antiinflammatory activity comprising a cosmetically effective amount of an extract of the leaf, green stalk, or flower of *Lycium halimifolium* as active ingredient together with a cosmetically acceptable topical vehicle or diluent.

2. The skin care composition defined in claim 1 comprising the extract of the leaf and green stalk of *Lycium halimifolium* as active ingredient.

3. The skin care composition defined in claim 1 comprising the extract of the flower of *Lycium halimifolium* as active ingredient.

4. The skin care composition defined in claim 1 comprising the extract of the leaf, green stalk, and flower of *Lycium halimifolium* as active ingredient.

5. A method of treating inflamed skin in a human in need of said treatment, which comprises the step of applying to the inflamed skin a cosmetically effective amount of a skin care composition in the form of a cream, body lotion, gel or body powder having keratolytic and antiinflammatory activity comprising an extract of the leaf, green stalk or flower of *Lycium halimifolium* as active ingredient together with a cosmetically acceptable topical vehicle or diluent.

6. The method of treating inflamed skin defined in claim 5 wherein the skin care composition comprises the extract of the leaf and green stalk of *Lycium halimifolium* as active ingredient.

7. The method of treating inflamed skin defined in claim 5 wherein the skin care composition comprises the extract of the flower of *Lycium halimifolium* as active ingredient.

8. The method of treating inflamed skin defined in claim 5 wherein the skin care composition comprises the extract of the leaf, green stalk, and flower of *Lycium halimifolium* as active ingredient.

* * * * *